United States Patent [19]

Chen et al.

[11] Patent Number: 5,569,799
[45] Date of Patent: Oct. 29, 1996

[54] PROCESS FOR THE PRODUCTION OF CHLORINATED HYDROCARBONS AND ALKENES

[76] Inventors: Wu-Chi Chen; Harvey R. Chen, both of 859 Brittmoore Rd., Houston, Tex. 77079-3601

[21] Appl. No.: 429,790

[22] Filed: Apr. 27, 1995

[51] Int. Cl.$^6$ ................................................. C07C 17/16
[52] U.S. Cl. ................................................. 570/261
[58] Field of Search ................................................. 570/261

[56] References Cited

U.S. PATENT DOCUMENTS

| | | | |
|---|---|---|---|
| 3,726,932 | 4/1973 | Mullin et al. | 570/261 |
| 3,937,744 | 2/1976 | Riegel | 570/261 |
| 4,105,702 | 8/1978 | Mullin et al. | 570/261 |

Primary Examiner—Alan Siegel

[57] ABSTRACT

The purpose of this invention is to describe a new process for the manufacture of monochloroethane and dichloroethanes which can be decomposed into ethylene ($C_2H_4$) and chloroethene ($C_2H_3Cl$), respectively, and recovered as products. This new process uses ethane ($C_2H_6$) and chlorinated ethenes or methanes as feedstocks. The distribution of the products may be adjusted so that either ethylene or chloroethene is the major product. The new process can also be used to produce propylene from propane, and butylene from butane.

16 Claims, 3 Drawing Sheets

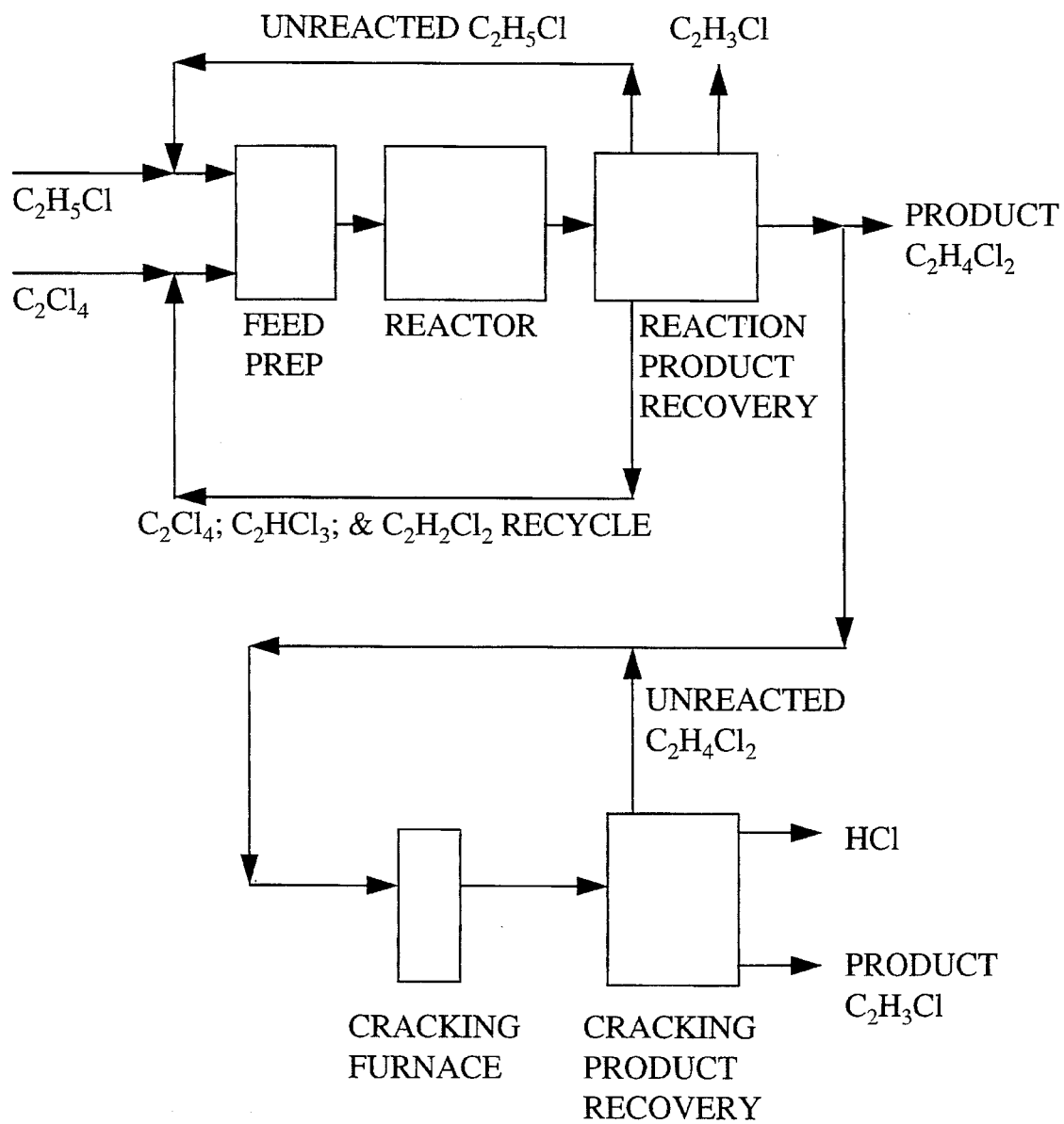
Figure 1: Block Diagram for Producing $C_2H_4Cl_2$ and $C_2H_3Cl$ from $C_2H_5Cl$ Figure 2: Block Diagram for Producing $C_2H_4$ and $C_2H_5Cl$ from $C_2H_6$
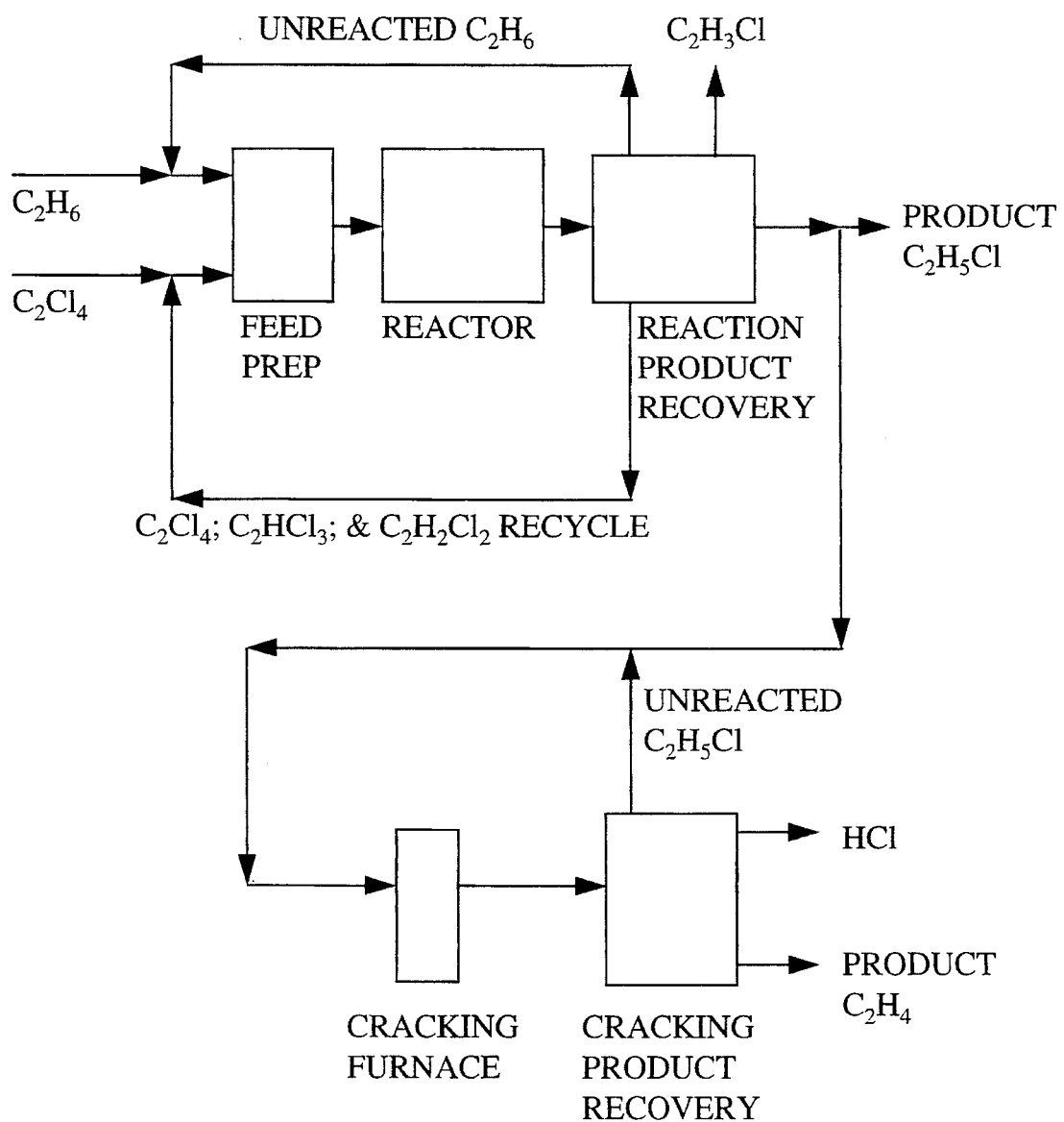

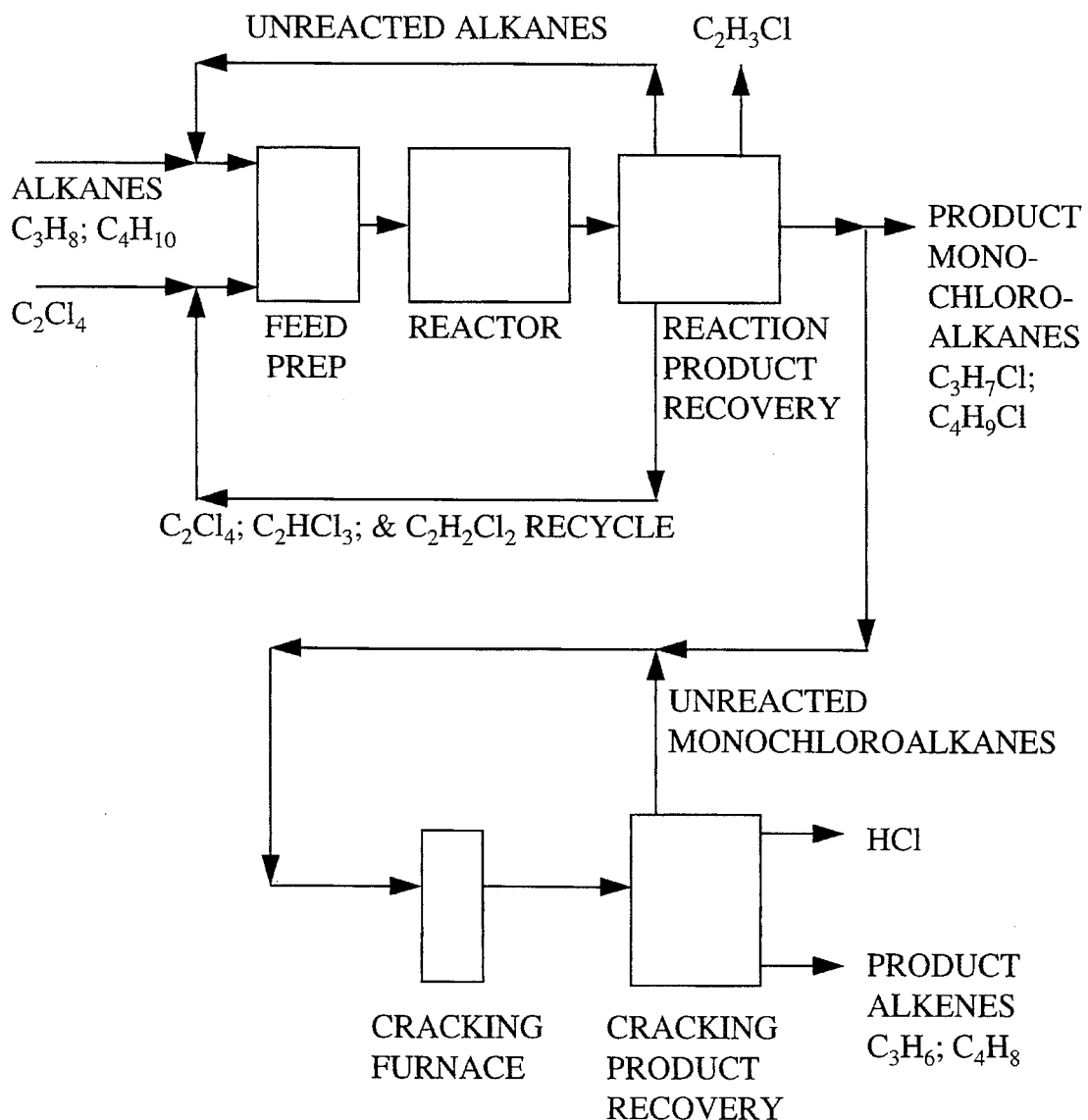
Figure 3: Block Diagram for Producing Monochloroalkanes and Alkenes from Alkanes

PROCESS FOR THE PRODUCTION OF CHLORINATED HYDROCARBONS AND ALKENES

FIELD OF THE INVENTION

This invention describes a new method for the manufacture of chloroethane ($C_2H_5Cl$), ethylene dichloride ($C_2H_4Cl_2$), ethylene ($C_2H_3Cl$), and chloroethene ($C_2H_3Cl$) from ethane ($C_2H_6$) using chlorinated ethenes or methanes as chlorinating agents. The principal products of this process are $C_2H_4$ and $C_2H_3Cl$. However, by adjusting feedstock ratios and recycling undesirable byproducts, the manufacture of a single product, such as ethylene or chloroethene, can be maximized. The new process can also be used to produce monochloropropanes and propylene from propane, and monochlorobutanes and butylenes from butane.

BACKGROUND OF THE INVENTION

Ethene ($C_2H_4$), commonly known as ethylene, is a major starting material in the petrochemical industries. It is used to produce high- and low- density polyethylenes, vinyl chloride monomer, and ethylene oxide, among others. In 1989, worldwide ethylene production capacity was about 58 million tons a year. U.S. capacity was about 17 million tons annually.

Ethylene is commercially produced by the cracking of ethane, propane, and heavy hydrocarbons such as naphtha at very high temperatures. Using ethane as an example, $$C_2H_6 \rightarrow C_2H_4 + H_2 \quad (1)$$

The reaction is highly endothermic, about 143 Kjoules/g-mole at 725° C. Steam is used to enhance cracking by reducing the partial pressure of the feedstock. Products are separated and recovered by cryogenic means. The whole operation is energy intensive. To achieve economy of scale, new plants are built with annual capacities of several hundred thousand tons each. A small improvement in ethylene production will have a great impact on the economics of the petrochemical industries.

Chloroethene, known as vinyl chloride monomer (VCM), is also a major commodity chemical in the world. It is used in the manufacture of polyvinyl chloride (PVC), one of the most important polymers. Commercially, two chemical reactions are used in the production of chloroethene, depending on the availability of the feedstock. The first reaction, used since the 1930's for large-scale production, involved acetylene and hydrogen chloride:

$$C_2H_2 + HCl \rightarrow C_2H_3Cl \quad (2)$$

Between the 1930's and the 1950's, most of the acetylene feedstock for this method was obtained by the reaction between calcium carbide and water. Because of the high cost and scarcity of acetylene, this method has been replaced by a process using more readily available ethylene as feedstock.

The second reaction, presently used in chloroethene production worldwide, involves the pyrolysis of ethylene dichloride, $C_2H_4Cl_2$ (EDC).

$$C_2H_4Cl_2 \rightarrow C_2H_3Cl + HCl \quad (3)$$

Ethylene dichloride is produced in a balanced process by both oxychlorination and direct chlorination of ethylene. In direct chlorination, ethylene is reacted with chlorine gas to produce ethylene dichloride. In oxychlorination, HCl produced in EDC pyrolysis is reacted with ethylene and oxygen to produce additional EDC and the byproduct water. If acetylene is available, hydrogen chloride produced from EDC cracking can be used to react with acetylene to produce chloroethene. In recent years efforts has been made to develop a commercial process using unpurified acetylene from advanced ethylene plants operating under more severe conditions.

The primary disadvantage present in this balanced VCM process is the cost of ethylene, which is substantially higher than that of ethane. The vent gases released from the oxychlorination step also contain more than 100 ppm of vinyl chloride, which has been shown to be an atmospheric health hazard. To minimize undesirable VCM emissions from the oxychlorination step, many plants use pure oxygen instead of air. Use of pure oxygen also improves the utilization of ethylene and hydrogen chloride. However, oxygen plants are expensive. In addition, cracking of EDC induces coke formation. Milder cracking conditions to minimize coking limits the conversion of EDC. Plants using this process generate significant amounts of chlorinated hydrocarbon waste that must undergo disposal treatments.

Ethylene is produced in many plants in the U.S. Gulf coast using ethane and propane as feedstocks. Major efforts have been made to produce chloroethene from ethane directly, saving the cost of manufacturing ethylene. U.S. Pat. No. 3,923,913 disclosed a process of chlorinating ethane at high temperature to produce VCM, ethylene, and chloroethane. Ethylene and chloroethane are further oxychlorinated to produce additional VCM U.S. Pat. Nos. 3,629,354, 3,658,933, and 3,658,934 disclosed processes of chlorinating ethane to produce ethylene and hydrogen chloride, which were then processed by traditional oxychlorination to 1,2-dichloroethane and subsequent cracking to VCM. U.S. Pat. Nos. 3,796,641, 3,920,764, and 3,935,288 disclosed processes to produce VCM using ethane and chlorine in a two-reactor molten salt system. Undesirable byproducts are recycled to extinction. Because of poor selectivity in ethane chlorination, most of these disclosed processes require high recyle rates for the feedstock.

Propene($C_3H_6$), commonly known as propylene, is also a major starting material in the petrochemical industries. It is used to produce polypropylene, acrylonitrile, and propylene oxide, among others. In 1990, worldwide propylene production capacity was about 30 million tons a year. U.S. capacity was about 10 million tons annually.

Propylene is commercially produced by the steam cracking of propane or liquid hydrocarbons such as naphtha at very high temperatures. However, propylene is usually considered a valuable byproduct of ethylene production because propane is decomposed into ethylene as well as propylene. In propylene production from propane, $$C_3H_8 \rightarrow C_3H_6 + H_2 \quad (4)$$

The reaction is highly endothermic, about 129 K J/g-mole at 725° C. Steam is used to enhance cracking by reducing the partial pressure of the feedstock. Propylene is also produced in refineries as a byproduct of the fluid-catalytic cracking and coking processes. It can also be produced as a main product by the thermal and catalytic dehydrogenation of propane. Both propane and propylene have very close boiling curves. In general, propylene is separated from propane and recovered by cryogenic means. Over 150 trays are used in a low temperature and high pressure distillation tower to recover polymer grade propylene. The whole operation is energy intensive.

Butene($C_4H_8$) is commonly known as butylene. Its main chemical use, which consumes only a small fraction of total available butylene, is for the production of butadiene. In the United States, a major portion of butylene is used as an alkylate feed. Outside the United States where liquid petroleum gas is not available, butylene is usually used as fuel. Butylene is commercially produced by the steam cracking, catalytic and thermal cracking, and dehydrogenation In steam cracking, and catalytic and thermal cracking, butylene is a byproduct of the ethylene production and refinery operation, respectively. In the dehydrogenation of butane, the conversion is limited by equilibrium consideration.

$$C_4H_{10} \rightarrow C_4H_8 + H_2 \tag{5}$$

The reaction is highly endothermic, about 120 K J/g-mole at 725° C. In product recovery, the mixture of butane and butylene isomers, which have very close boiling curves, are separated by complicated methods. Again, the whole operation is energy intensive.

It is therefore an object of the present invention to provide a new method for the production of $C_2H_5Cl$, $C_2H_4Cl_2$, ethylene, propylene, and chloroethene that minimizes or eliminates the disadvantages of the existing methods. Other objectives and advantages of the invention will become apparent from the following description and the accompanying drawings:

DESCRIPTION OF THE INVENTION

This new process manufactures $C_2H_5Cl$ and $C_2H_4Cl_2$ from ethane, monochloropropane from propane, and monochlorobutane from butane. Chlorinated ethenes and methanes, such as tetrachloroethene, trichloroethene, dichloroethenes, carbon tetrachloride, trichloromethane, dichloromethane, and monochloromethane, are used as chlorinating agents. Monochloroethane, dichloroethanes, monochloropropane, and monochlorobutanes can also be considered as intermediate products, which subsequently are decomposed to produce ethylene, VCM, propylene, and butylenes, respectively. Hydrogen chloride, generated in this process, can be recovered and reacted with oxygen and hydrocarbons such as ethane to produce chlorinated ethenes for the process. Either elemental chlorine or chlorinated hydrocarbons such as highly chlorinated hydrocarbon waste can be used as the make-up chlorine source.

In this process, $C_2H_6$ is reacted with chlorinating agents, such as tetrachloroethene, trichloroethene, and dichloroethenes, to produce monochloroethane.

$$C_2H_6 + C_2Cl_4 \rightarrow C_2H_5Cl + C_2HCl_3 \tag{6}$$

$$C_2H_6 + C_2HCl_3 \rightarrow C_2H_5Cl + C_2H_2Cl_2 \tag{7}$$

and $$C_2H_6 + C_2H_2Cl_2 \rightarrow C_2H_5Cl + C_2H_3Cl \tag{8}$$

Using tetrachloroethene as the initial chlorinating agent, the overall reaction for equations (6), (7), and (8) is $$3\ C_2H_6 + C_2Cl_4 \rightarrow 3\ C_2H_5Cl + C_2H_3Cl \tag{9}$$

Monochloroethane can be recovered as a product. Alternately, it is considered an intermediate product, which is heated and cracked to produce ethylene as the major product of this new process.

$$C_2H_5Cl \rightarrow C_2H_4 + HCl \tag{10}$$

Reaction (10) is an endothermic reaction. At 425° C., the heat of reaction is about 72.8 KJ/g-mole, which is about half of the heat required in direct cracking of ethane.

Furthermore, monochloroethane can be reacted with chlorinated ethenes to produce dichloroethane.

$$C_2H_5Cl + C_2Cl_4 \rightarrow C_2H_4Cl_2 + C_2HCl_3 \tag{11}$$

$$C_2H_5Cl + C_2HCl_3 \rightarrow C_2H_4Cl_2 + C_2H_2Cl_2 \tag{12}$$

and $$C_2H_5Cl + C_2H_2Cl_2 \rightarrow C_2H_4Cl_2 + C_2H_3Cl \tag{13}$$

Dichloroethane is recovered as a product, or heated and cracked to produce chloroethene as the major product of this new process.

$$C_2H_4Cl_2 \rightarrow C_2H_3Cl + HCl \tag{14}$$

Chloroethene is also produced as a product when dichloroethenes are used as the chlorinating agents shown in equation (13).

Chloromethanes can also be used as the chlorinating agents to produce mono- and di-chloroethanes. The reactions are $$C_2H_6 + CH_xCl_{4-x} \rightarrow C_2H_5Cl + CH_{x+1}Cl_{4-x-1} \tag{15}$$

and $$C_2H_5Cl + CH_xCl_{4-x} \rightarrow C_2H_4Cl_2 + CH_{x+1}Cl_{4-x-1} \tag{16}$$

where x=0, 1, 2, or 3.

To produce propylene in this process, $C_3H_8$ is reacted with chlorinating agents, such as tetrachloroethene, trichloroethene, and dichloroethenes, to produce monochloropropanes.

$$C_3H_8 + C_2Cl_4 \rightarrow C_3H_7Cl + C_2HCl_3 \tag{17}$$

$$C_3H_8 + C_2HCl_3 \rightarrow C_3H_7Cl + C_2H_2Cl_2 \tag{18}$$

and $$C_3H_8 + C_2H_2Cl_2 \rightarrow C_3H_7Cl + C_2H_3Cl \tag{19}$$

Using tetrachloroethene as the initial chlorinating agent, the overall reaction for equations (17), (18), and (19) is $$C_3H_8 + C_2H_2Cl_2 \rightarrow C_3C_3H_7Cl + C_2H_3Cl \tag{20}$$

Monochloropropanes can be recovered as products or as intermediate products, which are heated and cracked to produce propylene as the major product of this new process.

$$C_3H_7Cl \rightarrow C_3H_7Cl \rightarrow C_3H_6 + HCl \tag{21}$$

Reaction (21) is an endothermic reaction. At 425° C., the heat of reaction is about 58.4 KJ/g-mole, which is also about half of the heat required in cracking propane into propylene.

Chloromethanes can also be used as the chlorinating agents to produce monochloropropanes. The reactions are $$C_3H_8 + CH_xCl_{4-x} \rightarrow C_3H_7Cl + CH_{x+1}Cl_{4-x-1} \tag{22}$$

where x=0, 1, 2, or 3.

To produce butylenes in this process, $C_4H_{10}$ is reacted with chlorinating agents, such as tetrachloroethene, trichloroethene, and dichloroethenes, to produce monochlorobutanes $$C_4H_{10} + C_2C_2Cl_4 \rightarrow C_4H_9Cl + C_2HCl_3 \tag{23}$$

$$C_4H_{10}+C_2HCl_3 \rightarrow C_4H_9Cl+C_2H_2Cl_2 \quad (24)$$

and $$C_4H_{10}+C_2H_2Cl_2 \rightarrow C_4H_9Cl+C_2H_3Cl \quad (25)$$

Using tetrachloroethene as the initial chlorinating agent, the overall reaction for equations (23), (24), and (25) is $$3\ C_4H_{10}+C_2Cl_4 \rightarrow 3\ C_4H_9Cl+C_2H_3Cl \quad (26)$$

Monochlorobutanes can be recovered as a product or as an intermediate product, which is heated and cracked to produce butylenes as the major products of this new process.

$$C_4H_9Cl \rightarrow C_4H_8+HCl \quad (27)$$

Reaction (27) is an endothermic reaction. At 425° C., the heat of reaction is between about 39 and 67 KJ/g-mole, depending on isomers used and produced. Again, this heat requirement is much smaller than that needed for cracking butane into butylenes.

Chloromethanes can also be used as the chlorinating agents to produce monochlorobutane. The reactions are $$C_4H_{10}+CH_xCl_{4-x} \rightarrow C_4H_9Cl+CH_{x+1}Cl_{4-x-1} \quad (28)$$

where $x=0, 1, 2,$ or $3$.

Hydrogen chloride produced in the pyrolysis of monochloroethane, dichloroethane, monochloropropanes, and monochlorobutanes, as shown in equations (10), (14), (21), and (27), respectively, is recovered. It is reacted with oxygen and hydrocarbons such as ethane to produce trichloroethene and tetrachloroethene for the new process. For example, the oxychlorination reaction is carried out as follows:

$$C_2H_6+4\ HCl+5/2\ O_2 \rightarrow C_2Cl_4+5\ H_2O \quad (29)$$

Chlorinated hydrocarbon waste, if available, can also be used in oxychlorination. In fact, undesirable byproducts generated in this new process can be used within the new process. Chlorinated hydrocarbons, such as dichloroethenes produced in equations (7), (12), (18), and (24) can also be used to manufacture tetrachloroethene or trichloroethene for the new process.

Make-up chlorine needed for this new process can be supplied as elemental chlorine, hydrogen chloride, or chlorinated hydrocarbon waste. If elemental chlorine is available, it can be used to react with ethane or monochloroethane to produce monochloroethane and dichloroethanes directly. It can also be used in oxychlorination to produce tetrachloroethene and trichloroethene.

The new process may be adjusted so that the appropriate combination of products can be manufactured. By recovering and cracking monochloroalkane, the process is a new alkene process, in which vinyl chloride monomer is a valuable byproduct. By recovering and cracking dichloroethane, the process is a dedicated VCM process.

There are several advantages in this new process. First of all, vinyl chloride monomer is manufactured from ethane without using ethylene as an intermediate feedstock. This represents a substantial savings in the cost of processing ethylene. Also, the transport of chlorine gas to distant vinyl chloride producers can be made in the form of $C_2Cl_4$ and $C_2HCl_3$, which are easier and safer to handle and ship. Another advantage is that chlorinated hydrocarbon waste byproducts generated in enormous quantities in other chlorinated hydrocarbon industries can be used as sources of carbon and chlorine for the production of $C_2Cl_4$ and $C_2HCl_3$ for this new process. Therefore, the new process provides an economically and ecologically important method for the disposal and utilization of waste byproducts from the chlorinated hydrocarbon industries.

In the new process, intermediate products, i.e. monochloro-ethane, -propanes, and -butanes are heated and cracked to produce ethylene, propylene, and butylenes, respectively, at lower temperatures and with smaller amount of heat of endothermic reaction than those needed in the conventional steam cracking processes. The new process represents substantial savings in energy requirements in the production of ethylene, propylene, and butylenes.

The new process is illustrated in greater detail in the attached three drawings. The process can be carried out at various pressures from 1 atm to 40 atm. However, operating pressure between 5 and 20 atm are preferred because high pressure operations reduce equipment sizes and improve product recovery.

Referring to the accompanying drawings, FIG. 1 is a block diagram for producing ethylene dichloride and vinyl chloride monomer from monochloroethane. FIG. 2 shows a block diagram for producing monochloroethane and ethylene from ethane. FIG. 3 presents a block diagram for producing monochloroalkane such as monochloro-propane or -butanes, and alkene such as propylene or butylenes from the corresponding alkane. Highly chlorinated ethenes are used as the chlorinating agents. Purge streams to remove the undesirable byproducts and impurities introduced in the feeds are not shown in the drawings. Carbon tetrachloride, which can also be used as the chlorinating agent as described in this invention, is also not shown in the drawings. Whether carbon tetrachloride or tetrachloroethene should be used as the chlorinating agent depends on the ease of product separation and overall process economics. Many other variations of the process will become apparent after following the description of this invention.

BRIEF DESCRIPTION OF DRAWINGS

FIGS. 1, 2, and 3 represent basically the same process with similar types of equipments. Various products are manufactured, depending on the feedstocks. The drawings show the areas of feed preparation, reactor, reaction product recovery, cracking furnace, and cracking product recovery. In the reaction and cracking product recovery areas, side streams which are not shown in the drawings are purged to remove undesirable byproducts and impurities. Highly chlorinated ethenes such as dichloroethenes and trichloroethene can be recovered as byproducts or recycled to the reactor.

In feed preparation area, chlorinating agent is combined with feedstock and recycled streams, and the resulting stream is then sent to the reactor. Monochloroethane, ethane, and alkane are shown as feedstocks in FIGS. 1, 2, and 3, respectively. The temperature within the reactor can be controlled by, for example, excess feed, heat exchangers, or reactor feed temperatures. In the reactor, reactions proceed to the desirable direction between 100° C. and 650° C. At extremely high temperatures above 650° C., excess amount of undesirable byproducts are generated due to cracking. At operating temperature much less than 100° C., the reaction rates would be too slow to be practical. The preferred operating temperature is between about 350° C. and about 550° C., where only a small amount of cracking occurs. Reaction at higher temperatures would require a shorter residence time to minimize tar formation; whereas lower temperatures would require catalysts to promote reactions.

Effluent from the reactor is sent to the reaction product recovery area for separation and purification. Sensible heat in the reactor effluent can be recovered for use in other areas of the process. The effluent from the reactor can be cooled with recirculating liquid stream in a quench tower and the resulting stream is purified to recover reaction products as byproducts or intermediate products. The drawings show that dichloroethenes and trichloroethene are recovered as byproducts which are recycled as chlorinating agents. Unreacted reagents recovered from the reaction product recovery area are recycled. FIGS. 1, 2, and 3 show that ethylene dichloride, monochloroethane, and monochloroalkane, respectively, are recovered as intermediate products.

In the drawings, intermediate products are sent to the cracking furnace and cracking product recovery areas to manufacture other valuable products. For the ease of product recovery, the feed to the cracking furnace should be as pure as practical. The cracking temperature is between about 300° C. and 750° C. Temperature much below 300 ° C. is not practical because of low cracking rates. Much above 750° C., excess tar formation occurs. In the cracking furnace, hydrogen chloride is produced. It is recovered in product recovery area. In an integrated plant which is not shown in the attached drawings, hydrogen chloride produced in this process can be used in an oxychlorination plant to produce tetrachloroethene and trichloroethene for the process. FIGS. 1, 2, and 3 show that vinyl chloride monomer, ethylene, and alkene, respectively, are produced and recovered by cracking corresponding intermediate products manufactured in the new process.

We claim:

1. A process for the manufacture of $C_2H_4Cl_2$ consisting essentially of
   (a) the reaction of $C_2H_5Cl$ with a chlorinating stream which contains a highly chlorinated ethene which is $C_2H_5Cl_2$, $C_2HCl_3$, or $C_2Hl_4$, to produce $C_2H_4Cl_2$ and a corresponding less chlorinated ethene, which is $C_2H_3Cl$, $C_2H_2Cl_2$, or $C_2HCl_3$, respectively, and
   (b) the separation of the effluent from the reaction in order to recover $C_2H_4Cl_2$ as a product, recover unreacted $C_2H_5Cl$ and highly chlorinated ethene for recycling, and recover the less chlorinated ethene as a byproduct.

2. A process according to claim 1 in which the reaction is operated at a temperature between about 100° C. and about 650° C. and at a pressure between about 1 atm absolute and about 40 atm absolute.

3. A process according to claim 1 in which said less chlorinated ethene is $C_2H_2Cl_2$ or $C_2HCl_3$, which is recycled and reacted with $C_2H_5Cl$ to produce additional $C_2H_4Cl_2$.

4. A process according to claim 1 in which said $C_2H_4Cl_2$ is heated and decomposed, at a temperature between about 300° C. and about 750° C. and at a pressure between about 1 atm absolute and about 40 atm absolute in order to produce $C_2H_3Cl$, which is recovered as a product, and to produce HCl, which is recovered and reacted with oxygen and hydrocarbons or chlorinated hydrocarbons to produce said highly chlorinated ethene for the process.

5. A process according to claim 1 in which said chlorinating stream contains $CCl_4$, which is reacted with $C_2H_5Cl$ to produce $C_2H_4Cl_2$ for recovery as a product, and to produce less chlorinated methanes, such as $CHCl_3$, $CH_2Cl_2$, $CH_3Cl$, or $CH_4$, which are recovered as products or recycled to the process to produce additional $C_2H_4Cl_2$.

6. A process for the manufacture of $C_2H_5Cl$ consisting essentially of
   (a) the reaction of $C_2H_6$ with a chlorinating stream which contains a highly chlorinated ethene, which is $C_2H_2Cl_2$, $C_2HCl_3$, or $C_2Cl_4$, to produce $C_2H_5Cl$ and a corresponding less chlorinated ethene, which is $C_2H_3Cl$, $C_2H_2Cl_2$, or $C_2HCl_3$, respectively, and
   (b) the separation of the effluent from the reaction in order to recover $C_2H_5Cl$ as a product, recover unreacted $C_2H_6$ and the highly chlorinated ethene for recycling, and recover the less chlorinated ethene as a byproduct.

7. A process according to claim 6 in which the reaction is operated at a temperature between about 100° C. and about 650° C. and at a pressure between about 1 atm absolute and about 40 atm absolute.

8. A process according to claim 6 in which said less chlorinated ethene is $C_2H_2Cl_2$ or $C_2HCl_3$, which is recycled and reacted with $C_2H_6$ to produce additional $C_2H_5Cl$.

9. A process according to claim 6 in which product $C_2H_5Cl$ is heated and decomposed, at a temperature between about 300° C. and about 750° C. and at a pressure between about 1 atm absolute and about 40 atm absolute, into $C_2H_4$, which is recovered as a product, and into HCl, which is recovered and reacted with oxygen and hydrocarbons or chlorinated hydrocarbons to produce said highly chlorinated ethene for the process.

10. A process according to claim 6 in which $C_2H_5Cl$ is further reacted and chlorinated to produce $C_2H_4Cl_2$, which is recovered as a product or as an intermediate product which is further heated and decomposed into $C_2H_3Cl$, which is recovered as a product, and into HCl, which is recovered and reacted with oxygen and hydrocarbons or chlorinated hydrocarbons to produce said highly chlorinated ethene for the process.

11. A process according to claim 6 in which said chlorinating stream contains $CCl_4$, which is reacted with $C_2H_6$ to produce $C_2H_5Cl$, which is recovered as a product, and to produce less chlorinated methanes, such as $CHCl_3$, $CH_2Cl_2$, $CH_3Cl$, or $CH_4$, which are recovered as products or recycled to the process to produce additional $C_2H_5Cl$.

12. A process for the manufacture of monochloroalkane such as $C_3H_7Cl$ or $C_4H_9Cl$ consisting essentially of
   (a) the reaction of alkane which is $C_3H_8$ or $C_4H_{10}$ with a chlorinating stream which contains a highly chlorinated ethene, which is $C_2H_2Cl_2$, $C_2HCl_3$, or $C_2Cl_4$, to produce said monochloroalkane and a corresponding less chlorinated ethene, such as $C_2H_3Cl$, $C_2H_2Cl_2$, or $C_2HCl_3$, respectively, and
   (b) the separation of the effluent from the reaction in order to recover said monochloroalkane as a product, recover unreacted alkane and the highly chlorinated ethene for recycling, and recover the less chlorinated ethene as a byproduct.

13. A process according to claim 12 in which the reaction is operated at a temperature between about 100° C. and about 650° C. and at a pressure between about 1 atm absolute and about 40 atm absolute.

14. A process according to claim 12 in which said less chlorinated ethene is $C_2H_2Cl_2$ or $C_2HCl_3$, which is recycled and reacted with said alkane to produce additional monochloroalkane.

15. A process according to claim 12 in which said monochloroalkane is heated and decomposed, at a temperature between about 300° C. and about 750° C. and at a pressure between about 1 atm absolute and about 40 atm absolute, into corresponding alkene, which is recovered as a product, and into HCl, which is recovered and reacted with oxygen and hydrocarbons or chlorinated hydrocarbons to produce said highly chlorinated ethene for the process.

16. A process according to claim 12 in which said chlorinating stream contains $CCl_4$ which is reacted with said alkane to produce corresponding monochloroalkane, which is recovered as a product, and to produce less chlorinated methanes, such as $CHCl_3$, $CH_2Cl_2$, $CH_3Cl$, or $CH_4$, which are recovered as products or recycled to the process to produce additional monochloroalkane.

* * * * *